(12) United States Patent  
Zhang et al.

(10) Patent No.: US 8,735,831 B2  
(45) Date of Patent: May 27, 2014

(54) TRIGGER METHODS IN NUCLEAR MEDICAL IMAGING

(71) Applicant: Siemens Medical Solutions USA, Inc., Malvern, PA (US)

(72) Inventors: Nan Zhang, Knoxville, TN (US); Matthias J. Schmand, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 84 days.

(21) Appl. No.: 13/633,189

(22) Filed: Oct. 2, 2012

(65) Prior Publication Data

US 2013/0087710 A1    Apr. 11, 2013

Related U.S. Application Data

(60) Provisional application No. 61/543,856, filed on Oct. 6, 2011.

(51) Int. Cl.
*G01T 1/20* (2006.01)
*G01T 1/24* (2006.01)
*A61B 6/00* (2006.01)

(52) U.S. Cl.
CPC . *G01T 1/20* (2013.01); *G01T 1/249* (2013.01); *A61B 6/5205* (2013.01)
USPC ...................................... 250/362; 250/363.03

(58) Field of Classification Search
CPC ......... G01T 1/2985; G01T 1/164; G01T 7/00; G01T 1/1663; G01T 1/172; G01T 1/249; A61B 6/037; A61B 6/5205
USPC ........................................................ 250/362
See application file for complete search history.

(56) References Cited

U.S. PATENT DOCUMENTS

2002/0145115 A1* 10/2002 Nygard et al. ........... 250/370.09
2010/0078569 A1*  4/2010 Jarron et al. ............. 250/363.04

* cited by examiner

*Primary Examiner* — Marcus Taningco
(74) *Attorney, Agent, or Firm* — Peter Kendall (57) ABSTRACT

Disclosed herein are a system, method, and computer-readable storage medium for determining a time pickoff for both digital and analog photomultiplier circuits. Rather than basing time pickoff on the leading edge of a photomultiplier signal crossing a threshold or the first signal from a digital photomultiplier, a method for more accurate time calculations is disclosed. The system searches for peak values associated with the signal using differentiation, peak hold searching, and Gaussian distributions. Based on these calculations and comparisons, a more accurate time pickoff is determined.

12 Claims, 6 Drawing Sheets

TRIGGER METHODS IN NUCLEAR MEDICAL IMAGING

CROSS-REFERENCE TO RELATED APPLICATION

This application claims benefit of U.S. Provisional Application No. 61/543,856, filed on Oct. 6, 2011, the entire disclosure of which is hereby incorporated by reference.

TECHNICAL FIELD

The present invention concerns trigger methods in nuclear medical imaging such as Positron Emission Tomography (PET) or Single Photo Emission Computed Tomography (SPECT) scanners.

BACKGROUND

Figure 1:
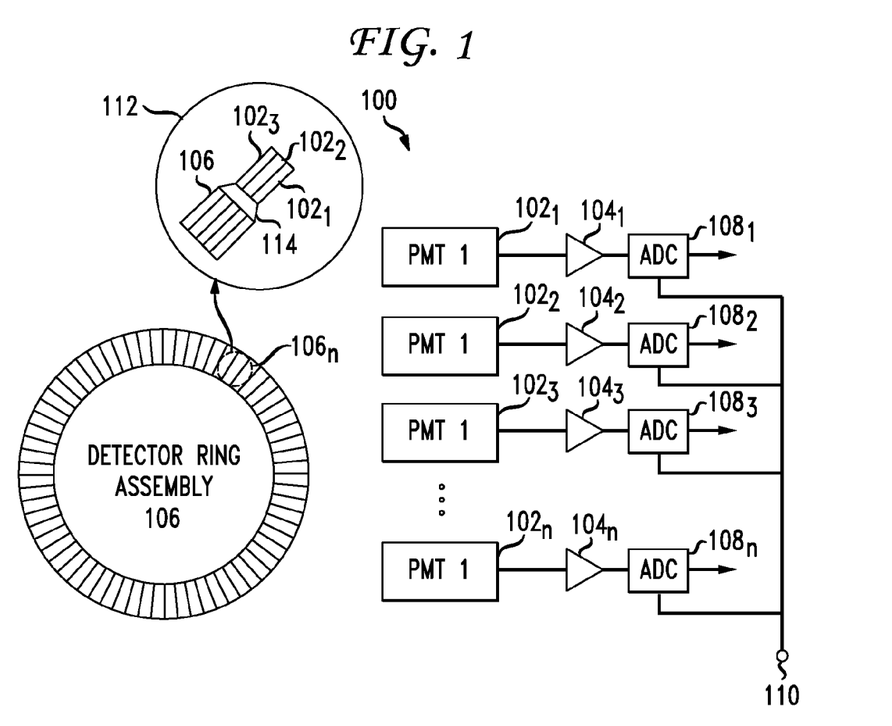
FIG. 1 illustrates a conventional detector ring assembly with associated detector circuitry of a conventional PET scanner.

In the field of nuclear medical imaging technology, which includes PET imaging detector 100, as illustrated in FIG. 1, an array of radiation sensors, such as plurality of scintillators 106 and associated photosensors 102$_n$, such as photomultiplier tubes (PMTs), avalanche photodiodes (APDs), or silicon photomultipliers (SiPMs) are usually arranged in a circle of a detector ring 106. Such a detector ring 106 surrounds a subject to be scanned. To conduct a so-called PET scan, a short-lived radioisotope, which decays by emitting a positron, is injected usually into the blood circulation of a living subject. After the metabolically active molecule becomes concentrated in tissues of interest, the research subject or patient is placed in the imaging scanner. The most commonly-used metabolically active molecule for this purpose is fluorodeoxyglucose (FDG), a sugar, which has a half life of 110 minutes. Note that other radiation sensors, such as solid state detectors could be used in the place of scintillators and photosensors.

As the radioisotope undergoes positron emission decay, it emits a positron, the antimatter counterpart of an electron. After traveling up to a few millimeters, the positron encounters and annihilates with an electron, producing a pair of gamma photons moving in almost opposite directions. These are detected when they reach one of a plurality of scintillation crystals in the scanning device, creating a burst of light detected by an array of photosensors. These bursts of light from a scintillator, such as Lutetium Orthosilicate (LSO) and Bismuth Germanate (BGO), have an intrinsic shape with a fast rising edge followed by a slow falling edge. The signals can be estimated as a function of:

$$V_o(t) \approx A_1 \cdot m_0 \cdot \left( \frac{1}{\tau_1} \cdot e^{-t/\tau_1} - \frac{1}{\tau_0} \cdot e^{-t/\tau_0} \right) \quad (1)$$

where $\tau_0$ is the characteristic scintillator decay time constant; and $\tau_1$ is mainly determined by the characteristics of the photosensor (such as PMT, APD, or SiPM), the open-loop gain of the first amplifier in the front-end electronics, and the input capacitance. When $\tau_0 \gg \tau_1$ (which are the cases for LSO and BGO crystals), $\tau_1$ dominates the rising edge of the pulse, and $\tau_0$ dominates the falling edge.

FIG. 1 illustrates a block diagram of the typical architecture of detectors and associated analog-to-digital-converters in a conventional system. Each matrix of photodetectors 112 produces a plurality of signals that can be processed to generate an image from a plurality of scintillation events that are detected by a photosensor 102. The photosensors 102 may be coupled to scintillators 106 through a lightguide 114. To determine the location of a detected annihilation, the system needs to accurately measure the timing and energy of both of the pair of oppositely traveling detected photons. Consequently a high amount of data has to be produced by the respective measurement circuits.

For example, as shown on the right side of FIG. 1, each scintillator has an associated matrix of detectors, such as photosensors 102$_1$ ... 102$_n$, in this example are PMTs for illustration. Each signal of each PMT 102$_1$ ... 102$_n$ is first amplified by, for example, associated preamplifiers/buffers 104$_1$ ... 104$_n$. The output signal of preamplifier/buffers 104$_1$ ... 104$_n$ can then be converted concurrently into discrete-time digital signals by associated analog-to-digital converters (ADC) 108$_1$ ... 108$_n$. A sampling clock for each ADC be can provided at terminal 110. In this example, this digital processing architecture uses n independent ADC signals with peripheral circuitry to concurrently sample each of n photosensor signals per block.

The Laplace transfer-function of the signal described by Eq. 1 is:

$$H(s) = \frac{A_1}{\tau_1} \cdot \frac{s}{\left(s + \frac{1}{\tau_0}\right) \cdot \left(s + \frac{1}{\tau_1}\right)} \quad (2)$$

As can be seen in Eq. 2, the falling edge of the scintillation signal is a first-order exponential decay function, so the shape of the signal is always unipolar—it is either positive or negative depending on the polarity chosen for the sensor analog electronics. Based on a time recorded for when the scintillation signal reaches a threshold value, the system can determine the location of positron emission. Because the detection systems often filter the scintillation signal prior to comparing the signal to the threshold, a "time-walk" can occur, reducing the precision of the positron emission measurement. A time-walk is the shift in time between when the non-filtered signal crosses a threshold and when a filtered signal crosses the threshold, and can be caused either by processing delays and/or by a difference in the filtered pulse height.

Figure 2:
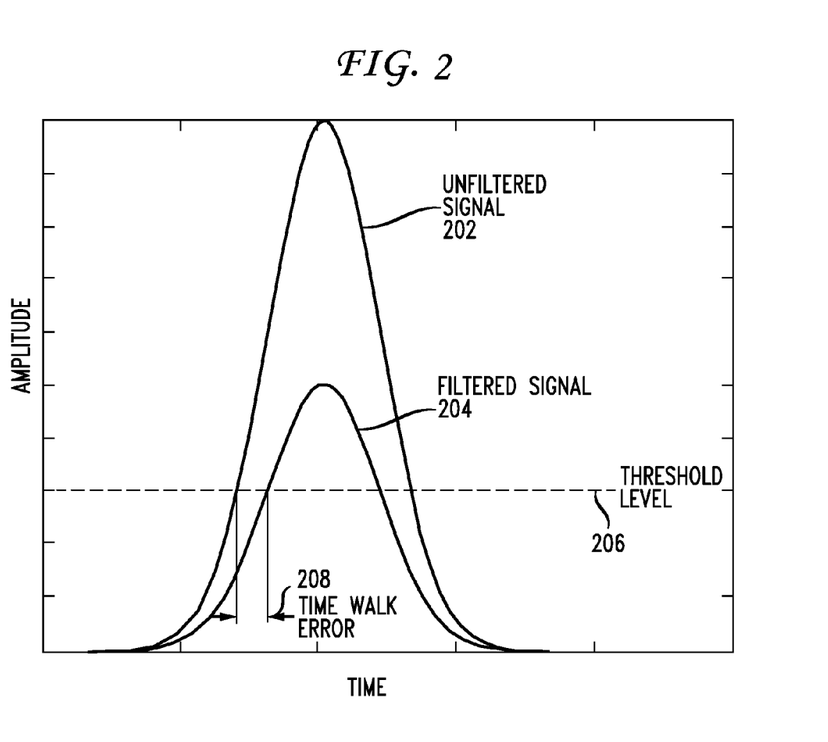
FIG. 2 illustrates an example of time-walk error.

FIG. 2 illustrates an example of time-walk error. In FIG. 2, the system receives an unfiltered signal 202, which the system then processes to yield a filtered signal 204. As illustrated, the filtered signal 204 normally has a lower peak value than the unfiltered signal 202. The difference between when the unfiltered signal 202 would have crossed a threshold 206 and when the filtered signal 204 crosses the threshold 206 is known as the time-walk error 208. Reducing this error can improve precision in recording positron emission measurements.

SUMMARY

To correctly determine a time pickoff, or an improved time measurement for positron emissions, a system, circuit, apparatus, device, or method can employ the techniques disclosed herein. The improvements disclosed herein, in providing more accurate positron emission measurements, allow for greater detail and improved diagnostics. In particular, they compensate for time-walk in conventional leading edge (LE) trigger methods and improve signal-to-noise ratio (SNR) emphasized in slope-to-noise ratio. A system configured according to this disclosure receives a signal from a scintillator and/or photosensor. Examples of these devices include standard PhotoMultiplier Tubes (PMT) and passive-quenching Silicon PhotoMultipliers (aSiPM) photosensors. The signal initially has a bell-curve, rising to a peak and falling back down. The first edge of the bell curve is referred to as the Relative Leading Edge (RLE).

Upon receiving the signal, or current pulse, the signal is first split into two channels. The first channel delays the signal, then shapes it, prior to submitting it to a comparator. The second channel filters the signal, takes the $1^{st}$ derivative, then performs a peak detection and hold analysis. This results in a slew-rate point indicating the maximum rate of change of the signal, output as a voltage. A fraction (or percentage) of this slew-rate voltage is selected as a trigger value, and is similarly submitted to the comparator. As an example, this can shift the trigger to a point further along the bell-curve of the signal, such as the signal peak, rather than during the rise time. In other instances, the trigger will be closer to the noise-floor.

This trigger value is "relative" to the slew-rate point. Therefore pulse amplitude variance and baseline fluctuations can be compensated accordingly. In addition, time-walk can be reduced compared to other LE trigger methods. In addition, the time requirements to determine if the scintillation signal meets the relative trigger are eased as compared to previous LE trigger methods. This process can be performed by both analog and digital circuits.

With photosensors which contain pre-determined triggers, such as digital mode SiPM (dSiPM) and single-photon-avalanche-diode (SPAD) sensors, the sensor itself determines when to change output from a binary "0" to a binary "1," indicating reception of a photon. While the circuit using pre-determined trigger photosensors only sees a "0" or "1," the delays and errors in timing of analog circuits still exist, despite the circuit only receiving a binary representation. As with analog circuits, the method disclosed herein can provide an improved positron emission time to systems utilizing these digital, avalanche, or other pre-determined trigger sensors.

Rather than calculating an analog voltage level to define the trigger level, systems using digital photosensors can delay collection of photon data for a period of time. This delayed time is equivalent to, or approximately equal to, the time for finding the slew-rate point in analog circuits (Eq. 3).

$$t_D \approx t_{SR} \quad (3)$$

After the delay, the system records the trigger times of subsequent photon triggers in a time period. For example, the system will record trigger times of photons detected for a time period corresponding to $[(t_0+t_D), (t_0+t_D+\Delta t)]$, where $t_0$ represents the initial photon detection point, $t_D$ represents the time delay before collection begins, and $\Delta t$ represents the interval during which trigger times are collected. After collecting n time marks of $(t_1, t_2, \ldots, t_n)$, the system estimates the time-pickoff using statistical methods. In certain configuration, the system performs a histogram of $(t_1, t_2, \ldots, t_n)$ to a Gaussian shape, then sets the peak position as the time-pickoff point ($\mu$ in Eq. 4).

$$f_{normalized}(t) = e^{-\frac{(t-\mu)^2}{2\sigma^2}} \quad (4)$$

If this calculation is too complex for the system, given either processing or time restraints, the estimated time-pickoff can instead simply be the average of $(t_1, t_2, \ldots, t_n)$.

DETAILED DESCRIPTION

A system, method, and computer-readable media are disclosed which improve time-pickoff in nuclear medical imaging. Various embodiments of the disclosure are described in detail below. While specific implementations are described, it should be understood that this is done for illustration purposes only. Other components and configurations may be used without parting from the spirit and scope of the disclosure.

An exemplary system includes a general-purpose computing device, including a processing unit (CPU or processor) and a system bus that couples various system components including the system memory such as read only memory (ROM) and random access memory (RAM) to the processor. The system can include a cache of high speed memory connected directly with, in close proximity to, or integrated as part of the processor. The system copies data from the memory and/or the storage device to the cache for quick access by the processor. In this way, the cache provides a performance boost that avoids processor delays while waiting for data. These and other modules can control or be configured to control the processor to perform various actions. Other system memory may be available for use as well. The memory can include multiple different types of memory with different performance characteristics. It can be appreciated that the disclosure may operate on a computing device with more than one processor or on a group or cluster of computing devices networked together to provide greater processing capability. The processor can include any general purpose processor and a hardware module or software module, configured to control the processor as well as a special-purpose processor where software instructions are incorporated into the actual processor design. The processor may essentially be a completely self-contained computing system, containing multiple cores or processors, a bus, memory controller, cache, etc. A multi-core processor may be symmetric or asymmetric.

The system bus may be any of several types of bus structures including a memory bus or memory controller, a peripheral bus, and a local bus using any of a variety of bus architectures. A basic input/output (BIOS) stored in ROM or the like, may provide the basic routine that helps to transfer information between elements within the computing device, such as during start-up. The computing device further includes storage devices such as a hard disk drive, a magnetic disk drive, an optical disk drive, tape drive or the like. The storage device can include software modules for controlling the processor. Other hardware or software modules are contemplated. The storage device is connected to the system bus by a drive interface. The drives and the associated computer-readable storage media provide nonvolatile storage of computer-readable instructions, data structures, program modules and other data for the computing device. In one aspect, a hardware module that performs a particular function includes the software component stored in a tangible computer-readable storage medium in connection with the necessary hardware components, such as the processor, bus, display, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device is a small, handheld computing device, a desktop computer, or a computer server.

Although the exemplary embodiment described herein employs the hard disk, other types of computer-readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment. Tangible computer-readable storage media expressly exclude media such as energy, carrier signals, electromagnetic waves, and signals per se.

To enable user interaction with the computing device, an input device represents any number of input mechanisms, such as a microphone for speech, a touch-sensitive screen for gesture or graphical input, keyboard, mouse, motion input, speech and so forth. An output device can also be one or more of a number of output mechanisms known to those of skill in the art. In some instances, multimodal systems enable a user to provide multiple types of input to communicate with the computing device. The communications interface generally governs and manages the user input and system output. There is no restriction on operating on any particular hardware arrangement and therefore the basic features here may easily be substituted for improved hardware or firmware arrangements as they are developed.

Having described an exemplary system or computing device, we provide a detailed description of the disclosed invention. We begin by considering FIG. 3. As a radioisotope undergoes positron emission decay, it emits a positron. When the positron collides with and annihilates an electron, pair of gamma photons are produced moving in almost opposite directions. Each photon is detected by a scintillator/photosensor 302. Upon detecting the photon, the scintillator/photosensor 302 generates a signal $f(t)$ 304. As stated above, Eq. 1 provides an example of an equation describing this signal $f(t)$ 304.

Figure 3:
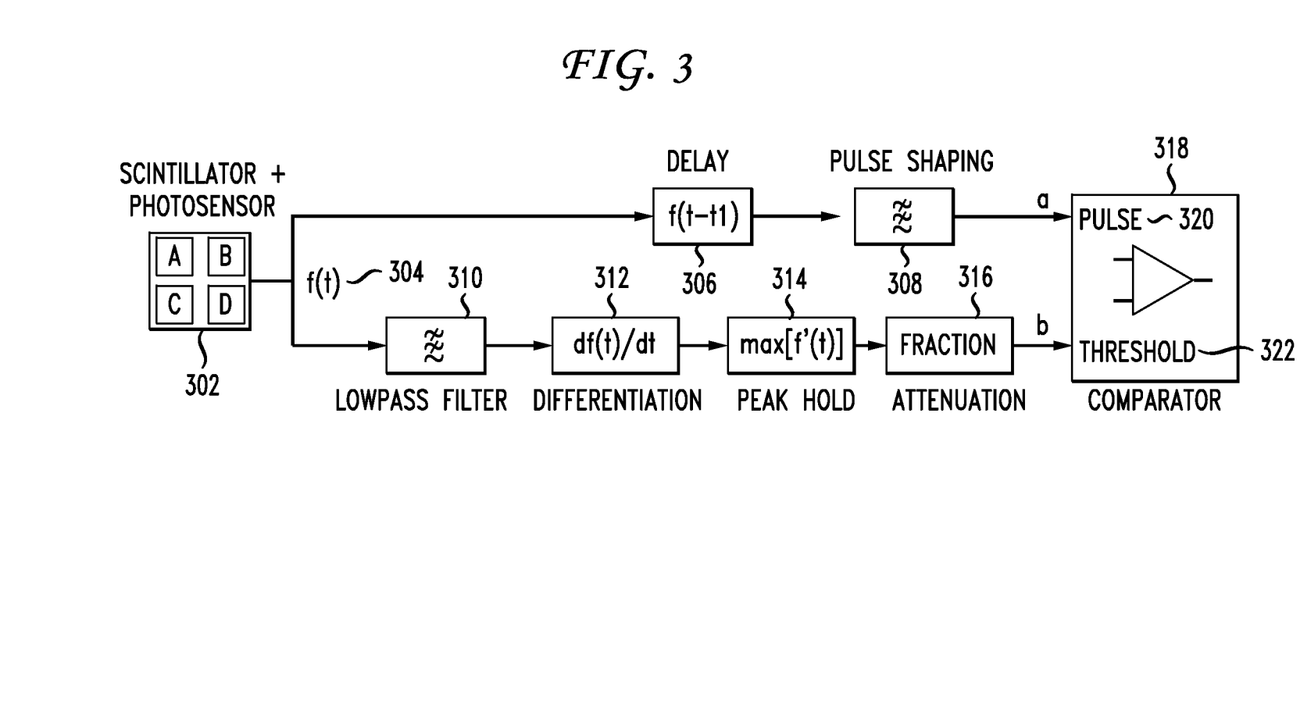
FIG. 3 illustrates an analog embodiment in accordance with the present invention.

Signal $f(t)$ 304 is processed along two paths, or channels. On the first channel, the signal is first delayed 306. The amount of time associated with this delay 306 can be predetermined, or can vary depending on specific circumstances or needs of the system. Where the overall method takes 2 ns, this initial delay 306 could be 0.5 ns. After storing and retrieving, or otherwise delaying the signal, the signal is then shaped 308. This pulse shaping can normally be a low-pass filter, although other forms of filtering or shaping are similarly possible. For example, the shaping could be a high-pass filter, a band-pass filter, an amplifier, an attenuator, etc. This modified signal (pulse), signal "a" of the first path, is then passed to an input 320 of a comparator 318. This input 320 can be an inverting input, a non-inverting input, or other form of input to the comparator 318. The comparator 318 can be a fast-comparator or another form of comparator.

On the second path, the signal $f(t)$ 304 is first shaped 310. Generally, this shaping 310 will be a lowpass filter, however as with the first path other forms of filtering or shaping are within the scope of this disclosure. After filtering the signal, the slope or first derivative of the pulse is calculated at $[d(f)t/dt]$ 312. One purpose of the second path is to improve the SNR (signal mean/standard deviation of the pulse amplitude) without degrading this slope or derivative. Using this derivative, the second path signal then detects the peak and hold portion of the signal using the derivative at a peak and hold unit 314. This peak and hold unit 314 determines the slew-rate point, which is a voltage level indicating the maximum rate of change in voltage of the original function $f(t)$. This is often associated with the peak of the signal $f(t)$. A fraction of this slew-rate point is taken by an attenuator 316 to act as a trigger voltage, or threshold 322. For example, this trigger voltage might be $0.5v_{SR}$, where $v_{SR}$ is the slew-rate point voltage. This trigger voltage is input into the comparator 318 as input "b," and acts as a threshold 322 voltage when compared the modified signal (pulse) "a" 320. From this comparator 318 a time pickoff is determined, which is recorded as the time associated with positron emission.

Figure 4:
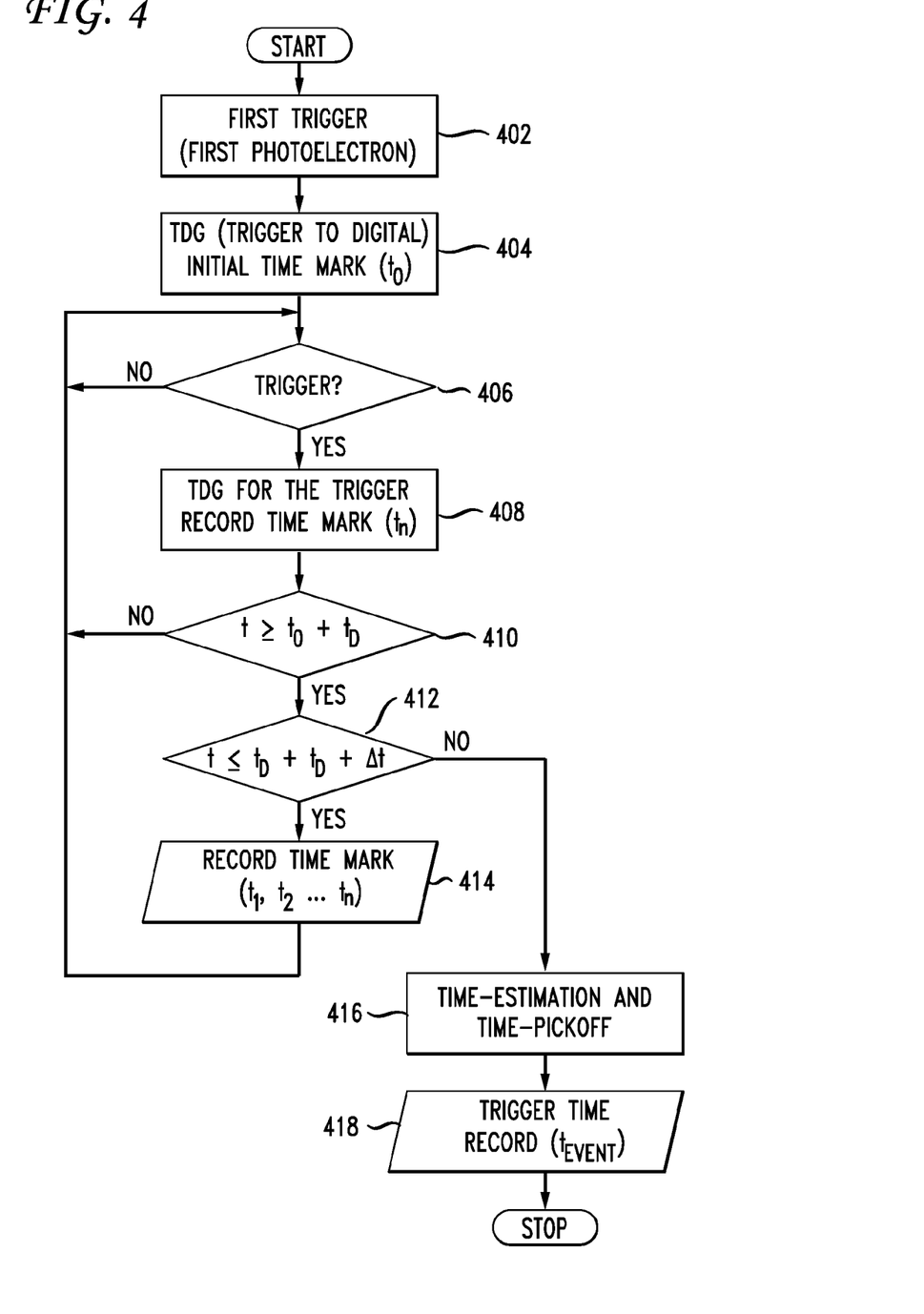
FIG. 4 illustrates a digital embodiment in accordance with the present invention.

While the circuit of FIG. 3 applies both to analog and digital circuits, the photosensors themselves are analog mode photosensors, including PMT and aSiPM sensors. FIG. 4 illustrates this same process applied to digital mode photosensors, such a digital mode SiPM or a SPAD. In these digital photosensors, normally the first photon seen by the SiPM microcell will trigger the cell and change the binary output from a "0" to a "1." In addition, normally the triggering edge of the 0 to 1 signal is translated to a digital time mark by a time-to-digital converter (TDC).

However, this time-mark starts when the very first "photon" is seen by the SiPM device—the very first cell "firing" from the hundreds of thousands of microcells contained within the photosensor. Whereas analog photosensors must have a certain level of detection to meet the threshold, the ability to digitally "OR" microcell output means that dSiPM and SPAD devices are "naturally" single photon detection devices. However, as indicated above, the time pickoff per this disclosure is often better obtained by being related to the slew-rate point, which is often the peak of the signal indicating photon reception.

To repeat the functionality of the analog configuration, the digital configuration therefore does not acquire the time pickoff from the trigger originated from the first photoelectron. Instead, the very first photon triggers (402) a microcell that generates a digital time mark $(t_0)$ (404). This is done by converting the 0 to 1 pulse "edge" to "digits" using a time-to-digital converter (TDC) (404). The TDC can be made using a dedicated hardware TDC Integrated Circuit (IC) or by using a "field-programmable gate array" (FPGA).

As additional microcells collect photons, they act as additional triggers (406), or additional binary signals. When the microcells receive the photons, they act as triggers (406) and are sent as binary signals from the digital photosensor to the system configured per this disclosure. The system determines a current time $(t_n)$ of each trigger received (408). However, the system then evaluates (410) if a specified amount of time, the "delay time," or $(t_D)$, has passed since reception of the initial photon trigger at $t_0$. This time delay acts as an adjustment to approximate finding the slew-rate point in the analog configuration. If not sufficient time has passed, the system continues to wait and receive additional signals from the various microcells. However, if the time delay, $t_D$, has passed (i.e., the time t is greater than or equal to $t_0+t_D$), then the system determines if the current time is within a collection interval $\Delta t$ (412).

If the time is within the interval $\Delta t$, the system records the time associated with that signal (414). During this interval, the system can collect a single time mark, or a set of time marks, such as $(t_1, t_2, \ldots t_n)$. As the system continues receiving triggers, eventually the collection interval $\Delta t$ will end. When the collection interval ends, the system performs a time-estimation and time-pickoff (416) using the time marks collected. Ideally, this time-estimation utilizes statistical methods to determine a Gaussian distribution using the time marks, then sets the peak position as the time-pickoff point. Equation (4) above describes such a Gaussian shape. When circumstances, such as time, processing power, or circumstances deem such a calculation too expensive or costly to implement, simpler methods such as averaging can also be used. The results of this calculation, the time-pickoff, are recorded as being associated with the positron emission in question (418).

Figure 5:
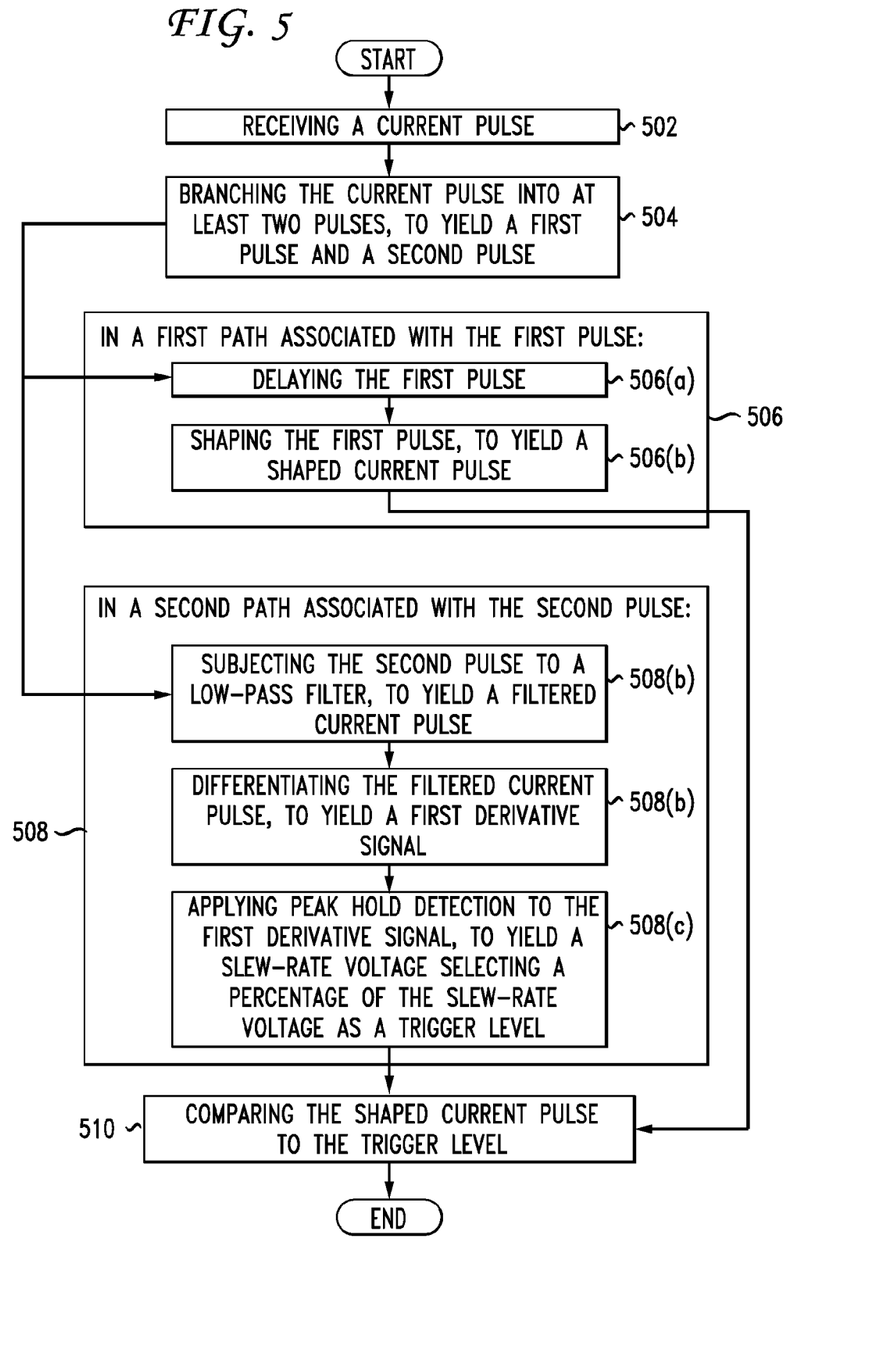
FIG. 5 illustrates a first method embodiment in accordance with the present invention.

FIG. 5 illustrates a first method in accordance with the invention. For the sake of clarity, the method is described in terms of an exemplary system configured to practice the method. The steps outlined herein are exemplary and can be implemented in any combination thereof, including combinations that exclude, add, or modify certain steps.

The system receives a current pulse (502). This current pulse can represent a scintillation signal directly from a photosensor, or can represent a signal indicating that scintillation has occurred. Alternatively, the pulse can be associated with an indication that a photon has been detected. Exemplary photosensors include analog mode photosensors, such as PMT and passive-quenching silicon-photomultiplier detectors. The current pulse is then branched into at least two pulses, to yield a first pulse and a second pulse (504). In a first path associated with the first pulse (506), the system delays the first pulse (506(*a*)). This delay can be accomplished by recording the first pulse in a memory, by an analog delay circuit, or by another other means for accomplishing a signal delay. After the delay time period ends, the first pulse is shaped, yielding a shaped current pulse (506(*b*)). This shaping can be accomplished via a low-pass filter, a high-pass filter, a band-pass filter, attenuation, amplification, or other shaping mechanisms.

In a second path associated with the second pulse (508), the system subjects the second pulse to a low-pass filter, to yield a filtered current pulse (508(*a*)). In alternative configurations, this can filter can be a high-pass filter, band-pass filter, attenuator, amplifier, or other waveform shaping mechanisms. The system takes the filtered current pulse and differentiates it, to yield a first derivative signal (508(*b*)). Other configuration can use only a single derivative signal, or can use multiple derivatives signal. The usage of "first derivative" however indicates that this is the first derivative of the filtered current pulse in a mathematical connotation. This first derivative signal is subjected to peak hold detection, to yield a slew-rate voltage, of which a percentage or fraction is selected as a trigger level (508(*c*)). Peak hold detection can occur as part of a separate unit, or module, or can be performed by a single processor performing other steps in this method. The peak hold detection identifies the peak voltage associated with the original signal, or alternatively, identifies an important signal feature which can act as a point representing positron emission time. The taking of a percentage of the slew point voltage for a trigger point can be any percentage, depending on specific needs of a given configuration. For example, certain configurations can set the percentage at 100%, whereas other can set the percentage at 1% or 50%. Upon calculating both the trigger level (508(*c*)) and shaping the first pulse (506(*b*)), the system compares the shaped current pulse to the trigger level (510). When the shaped current pulse meets the trigger level, a time is recorded representing the time pickoff associated with the emission of the positron and/or collection of photon. The system can then use this value for future diagnosis and calculations in medical imaging.

The method of FIG. 5 can be practiced using both analog and digital components. In addition, exemplary digital components include processors, FPGAs, integrated circuits, and ASIC chips.

Figure 6:
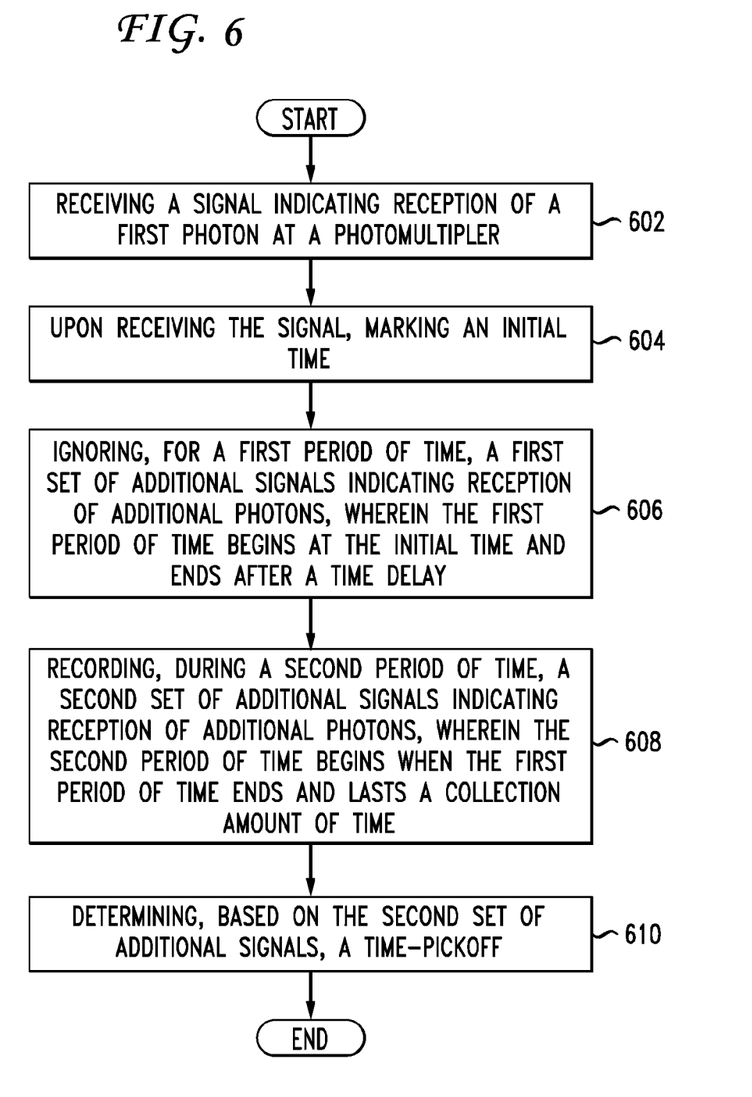
FIG. 6 illustrates a second method embodiment in accordance with the present invention.

FIG. 6 illustrates a second exemplary method embodiment. As with FIG. 5, FIG. 6 is described in terms of an exemplary system configured to practice the method. The steps outlined herein are exemplary and can be implemented in any combination thereof, including combinations that exclude, add, or modify certain steps.

In this method, the system receives a signal indicating reception of a first photon at a photomultiplier (602). Exemplary photomultipliers include digital mode enabled photomultipliers, such as an active-quenching silicon-photomultiplier or a single photon avalanche photodiode (SPAD). The signal can be pre-processed prior to reception by the system, or can be received directly from the photomultiplier. Upon receiving the signal, the system marks an initial time (604). From that initial time, the system ignores, for a first period of time, a first set of additional signals indicating reception of additional photons, wherein the first period of time begins at the initial time and ends after a time delay (606). The first set of additional signals can, in certain situations, be an empty set, meaning no signals will be detected during the time delay interval. In addition, the additional signals can, rather than representing additional photons, indicate unique microcells reaching a threshold value within the photomultiplier. In certain configurations, the time delay can be 2 ns, whereas in other configurations the amount of delay can change according to need.

Having waited a delay amount of time, the system begins recording, during a second period of time, a second set of additional signals indicating reception of additional photons, wherein the second period of time begins when the first period of time ends and lasts a collection amount of time (608). Again, the additional photons can represent signals from additional microcells within the photomultiplier. The collection amount of time represents an interval during which the system is recording times when the signals are received. These times should generally represent a bell curve, where the peak density would correspond to the peak amplitude of an analog photomultiplier. After the interval, the system determines, based on the second set of additional signals, a time-pickoff (610). This time pickoff represents an estimation of when the positron emission occurred and will be used for future calculations and diagnosis. Often, the time-pickoff corresponds to a peak in a Gaussian distribution, determined from the second set of additional signals through statistical analysis. The system can perform other statistical and data manipulations on the second set of data to shift the obtained time-pickoff should the described Gaussian peak not suffice.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. For example, while the disclosure focuses on PET applications, a person of ordinary skill in the art could, after reviewing this disclosure, apply the same principles to SPECT systems because the two modalities operate in a similar manner. In addition, other radiation sensors, such as solid state sensors, could be substituted for photosensors. The depicted and described embodiments of this disclosure are examples only, and are not exhaustive of the scope of the disclosure.

What is claimed is:

1. A nuclear imaging apparatus comprising:
an array of radiation sensors; and
analog circuitry which performs a method comprising:
   receiving a current pulse;
      branching the current pulse into at least two pulses, to yield a first pulse and a second pulse;
   in a first path associated with the first pulse:
      delaying the first pulse; and
      shaping the first pulse, to yield a shaped current pulse;
   in a second path associated with the second pulse:
      subjecting the second pulse to a low-pass filter, to yield a filtered current pulse;
      differentiating the filtered current pulse, to yield a first derivative signal; and
         applying peak hold detection to the first derivative signal, to yield a slew-rate voltage selecting a percentage of the slew-rate voltage as a trigger level; and
   comparing the shaped current pulse to the trigger level.

2. The nuclear imaging apparatus of claim 1, wherein the radiation sensor is at least one of a photomultiplier tube and a passive quenching silicon-photomultiplier.

3. The nuclear imaging apparatus of claim 1, wherein the analog circuitry comprises additional circuitry which results in the method further comprising recording a time associated with the current pulse based on the comparing of the shaped current pulse to the trigger level.

4. The nuclear imaging apparatus of claim 1, wherein the slew-rate voltage is associated with a peak-value of the current pulse.

5. The nuclear imaging apparatus of claim 1, wherein comparing the shaped current pulse to the trigger level comprises use of a comparator circuit.

6. The nuclear imaging apparatus of claim 5, wherein the shaped current pulse is applied to one of an inverting input of the comparator circuit and a non-inverting input of the comparator circuit.

7. A system of photoelectron triggering comprising:
a processor; and
a computer-readable storage medium having instructions stored which, when executed by the processor, cause the processor to perform a method comprising:
   receiving a current pulse;
      branching the current pulse into at least two pulses, to yield a first pulse and a second pulse;
   in a first path associated with the first pulse:
      delaying the first pulse; and
      shaping the first pulse, to yield a shaped current pulse;
   in a second path associated with the second pulse:
      subjecting the second pulse to a low-pass filter, to yield a filtered current pulse;
      differentiating the filtered current pulse, to yield a first derivative signal; and
         applying peak hold detection to the first derivative signal, to yield a slew-rate voltage selecting a percentage of the slew-rate voltage as a trigger level; and
   comparing the shaped current pulse to the trigger level.

8. The system of claim 7, wherein the radiation sensor is at least one of a photomultiplier tube and a passive quenching silicon-photomultiplier.

9. The system of claim 7, wherein the computer-readable medium has additional instructions stored which result in the method further comprising recording a time associated with the current pulse based on the comparing of the shaped current pulse to the trigger level.

10. The system of claim 7, wherein the slew-rate voltage is associated with a peak-value of the current pulse.

11. The system of claim 7, wherein comparing the shaped current pulse to the trigger level comprises use of a comparator circuit.

12. The system of claim 11, wherein the shaped current pulse is applied to one of an inverting input of the comparator circuit and a non-inverting input of the comparator circuit.

* * * * *